United States Patent [19]

Frigger

[11] Patent Number: 5,460,176

[45] Date of Patent: Oct. 24, 1995

[54] POSITIVE LOCKING CANNULA

[75] Inventor: David Frigger, Lake Forest, Calif.

[73] Assignee: Mallinckrodt Medical, Inc., St. Louis, Mo.

[21] Appl. No.: 189,529

[22] Filed: Jan. 31, 1994

[51] Int. Cl.⁶ .................................................. A61M 39/12
[52] U.S. Cl. ......................... 128/207.14; 128/202.29; 128/200.26; 128/912; 128/DIG. 26; 285/314; 439/290
[58] Field of Search ........................ 128/207.29, 207.14, 128/207.15, 207.16, 207.17, 200.26, 911, 912, DIG. 26; 604/45, 159, 178; 285/314, 86; 439/290, 291, 293, 310, 311, 128

[56] References Cited

U.S. PATENT DOCUMENTS

| 1,982,183 | 11/1934 | Tarbox | 285/86 |
| 3,169,529 | 2/1965 | Koenig | 128/207.14 |
| 4,033,353 | 7/1977 | LaRosa | 128/207.15 |
| 4,235,229 | 11/1980 | Ranford et al. | 128/207.15 |
| 4,684,156 | 8/1987 | Rhodes | 285/86 |
| 5,067,496 | 11/1991 | Eisele | 128/207.14 |
| 5,254,013 | 10/1993 | Tanaka | 285/86 |

Primary Examiner—Edgar S. Burr
Assistant Examiner—William J. Deane, Jr.
Attorney, Agent, or Firm—David A. Hey

[57] ABSTRACT

A positive locking device for connecting an inner cannula within an outer cannula to form a tracheostomy tube device. The tracheostomy device is provided with a connector head or connector body having ribs and or lips with associated catches disposed thereon. Cantilevered members with latch receiving members corresponding to the catches are provided on the component (connector or connector head) not having the rib or lip. Alternatively, catches may be associated with cantilevered members and latch receiving members with lips or ribs. Catches and latch receiving surfaces interlock and a securing component is fixed over the connector and connector head to create a positive lock.

11 Claims, 4 Drawing Sheets

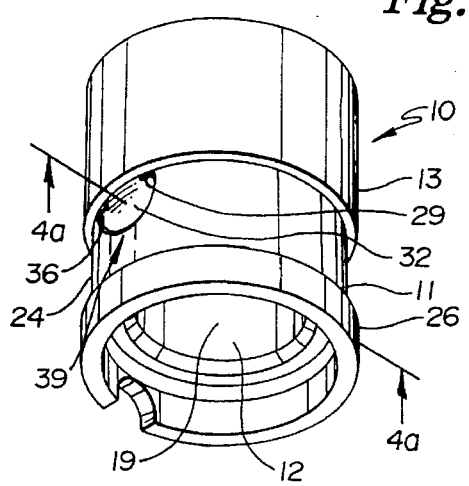
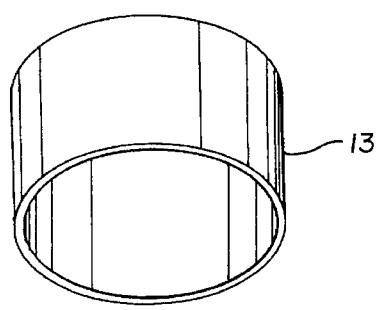
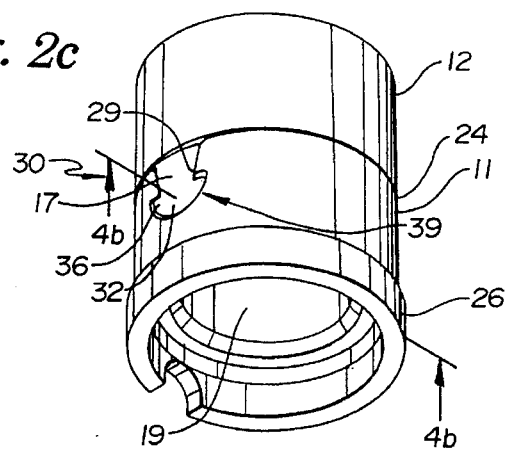
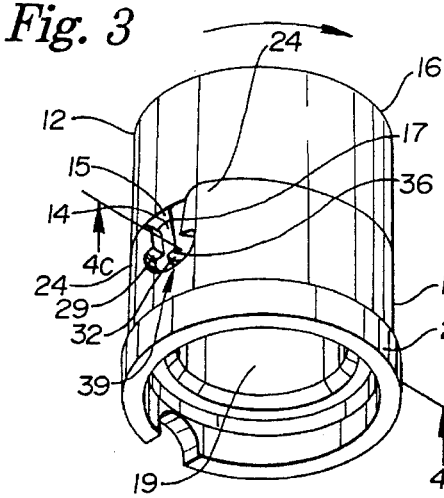
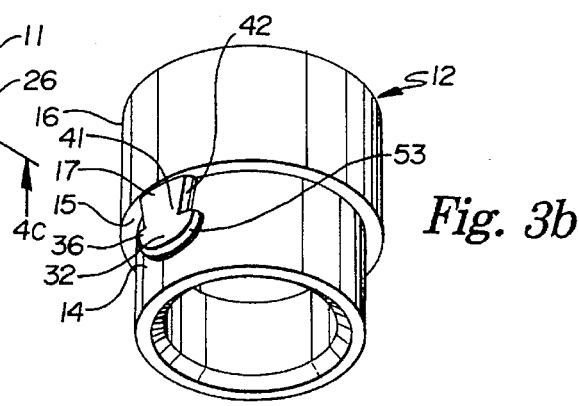
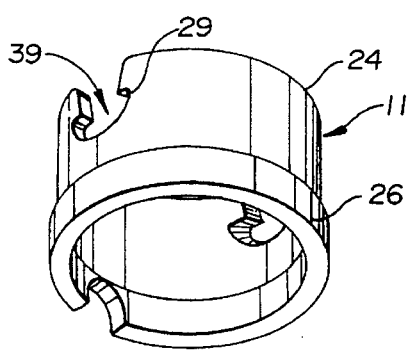

Fig. 4
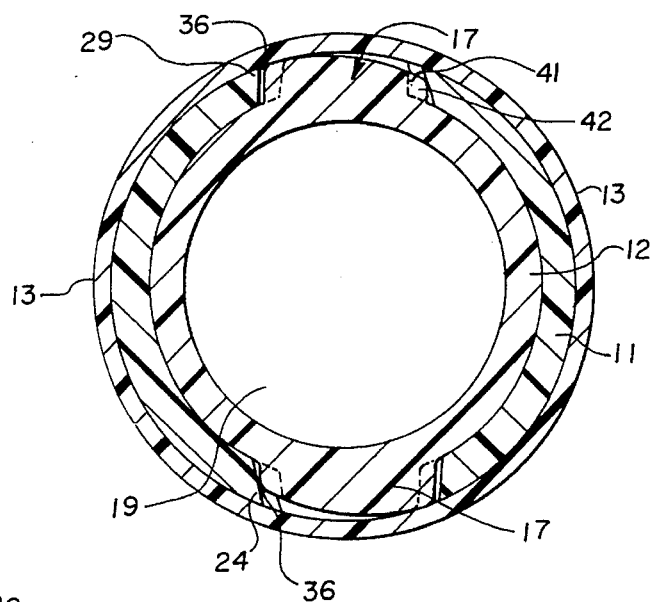
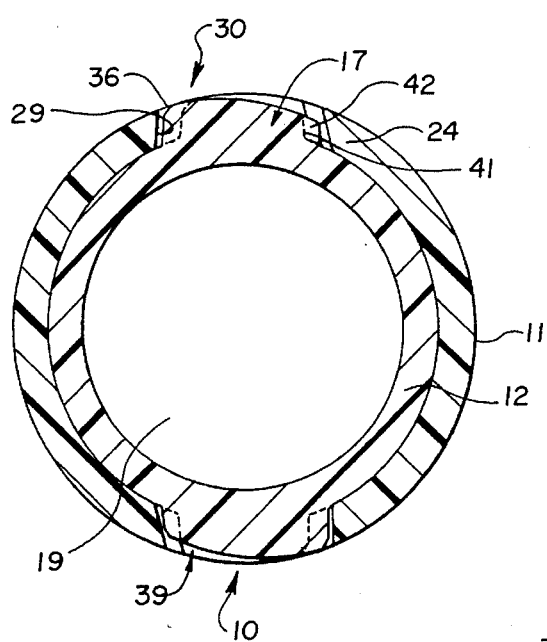
Fig. 4b
Fig. 4c
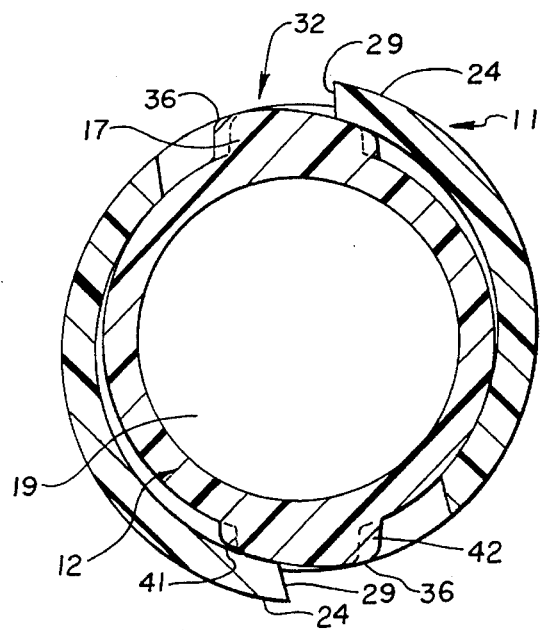

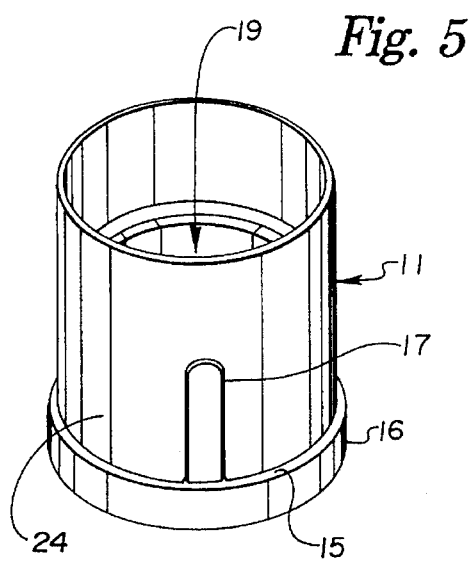
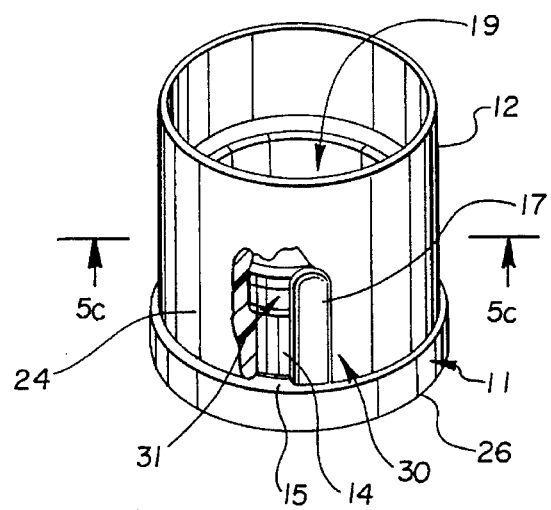
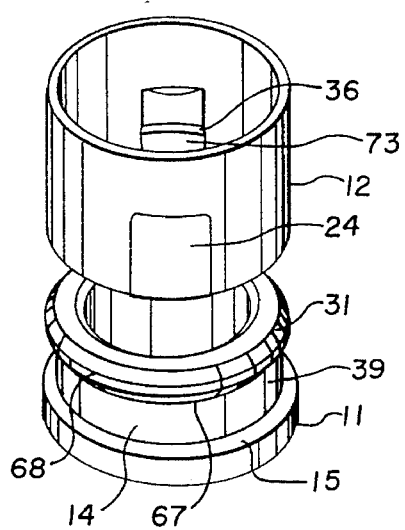
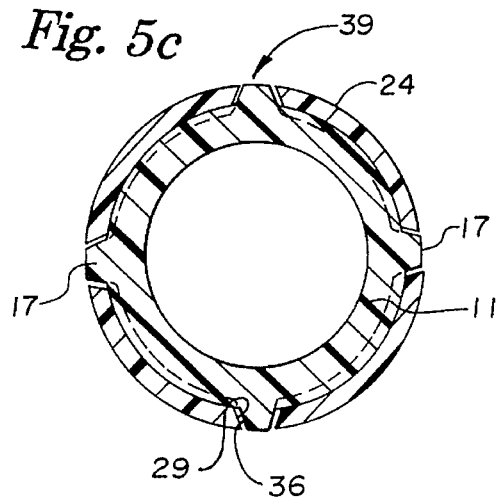
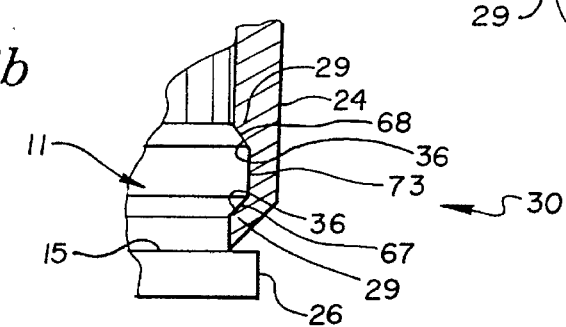

POSITIVE LOCKING CANNULA

BRIEF DESCRIPTION OF THE INVENTION

This invention relates to a breathing apparatus connection assembly for a tracheostomy tube assembly that employs positive locking of the connection between a connector head and a connector body.

BACKGROUND TO THE INVENTION

Tracheostomy tubes are used to assist a patient to breathe. The tube is inserted in a patient's throat through a puncture wound below an obstruction. When in place, the tube provides a direct connection between an oxygen or air source and the trachea.

A common type of tracheostomy tube is equipped with inner and outer cannulae; the inner cannula fitting within the outer cannula. The inner cannula is provided with a connector body while the outer cannula is provided with a connector head. The connector body and connector head interlock to secure the inner cannula within the outer cannula. A breathing apparatus connector slides over this connection to provide a complete air circuit.

The inner cannula is removable if obstructed. When the inner cannula is removed, the outer cannula maintains the oxygen or air path to the trachea. To assist in its removal, and to avoid discomfort to the patient, the disposable cannula should be easily detached from the outer cannula. Ease in detachment is particularly important where the patient is connected to a ventilator because it is likely that the patient is unable to breathe on his own while the changeover is accomplished.

Many tubes in the prior art employ manually clamping of the inner cannula to the outer cannula. Crandall, U.S. Pat. No. 4,009,720 employs a device with two clamps having short, cantilevered actuator arms attached to hooks. The clamps are connected to the disposable cannula and the actuator arms are substantially in the same plane as the connection point for the clamps. The clamp is operated by pressing the cantilevered actuator arms, thereby causing the hooks to rotate to an open position against the torque from a flexible hinge. Once the disposable cannula is properly inserted into the outer cannula, pressure is released and the hooks secure the cannulae together. To prevent breakage from an over-extension of the hinge, stops are provided for the clamps. Similar devices are disclosed in Crandall, et al., U.S. Pat. No. 3,639,624, Crandall et al., U.S. Pat. No. 4,135,505, Eisele, U.S. Pat. No. 5,067,496, and Abel, U.S. Pat. No. 5,067,515.

Other tubes employ friction-fit locking devices. U.S. Pat. No. 4,052,990 to Dodgson discloses a typical tubing adaptor that is assembled with an endotracheal tube such as a tracheostomy tube. The device comprises a molding having a cup shaped body portion with an internal stem. The stem has an outwardly flared lip. This lip is engaged by the tube to provide a friction fit without a positive locking connection. Consequently, this connector is subject to accidental disconnections.

While these clamps adequately secure the inner cannula to the outer cannula, accidental disconnections have occurred because the patient is capable of unfastening the inner cannula while the tracheostomy tube is connected to a ventilator or other breathing apparatus. It is desirable for devices connecting tracheal tubes and breathing apparatus or other oxygen or air sources be able to avoid accidental disconnection, even when subjected to aggressive manipulation by an active patient. There is a need for a locking system that prevents detachment of the cannulae, while at the same time, allows easy detachment of the inner cannula by the care giver.

THE INVENTION

This invention relates to an improvement in tracheostomy tube assemblies that employs inner and outer cannulae linked by a locking device. The improvement is a locking device for the inner and outer cannulae that prevents the patient from accidentally separating the inner cannula from the outer cannula when it is connected to a breathing apparatus.

A tracheal tube, such as an outer cannula, with the typical proximal and distal ends is provided with a connector head circumscribing its proximal end. The connector head provides an attaching surface for linkage to a readily detachable connector body. The connector body is locked to the connector head via interlocking catches, latch receiving surfaces, ribs and/or lips A securing component such as a breathing apparatus connector is fitted over the interlocked connector body and connector head to provide a positive locking device wherein the locked connector and connector head are held together in a fixed position through the positive pressure imposed on them by the securing component.

The connector body/connector head locking device comprises an interlocking male and female assembly. The connector body and connector head are locked together by joined catch and a latch receiving surface. The catch is located on either the connector head or connector body, and the latch receiving surface is located on the other of the connector body or connector head, to form an interlocking assembly. Either the connector body or the connector head is provided with a rib and/or a lip and whichever of the connector body or connector head that does not have the rib and/or lip is provided with at least one flexible cantilevered member capable of mounting the rib or lip and expanding the same sufficiently that the connector head and the connector body can be separated.

To facilitate disconnection, the ribs and lips have ramping surfaces such that when these elements are twisted or pulled along a vertical axis, they slide under the flexible cantilevered member(s), causing the member(s) to flex by riding on the ramped surface(s). Once the members have flexed, the interlocking catches and latch receiving surfaces are disengaged and no longer interlock by pulling the connector body from the connector head or vice versa. The connector body and connector head are easily separated.

To ensure against accidental disconnection, a securing component such as a breathing apparatus connector is fitted over the connector body and connector head to frictionally engage and lock the rib or lip of the connector body by providing pressure to hold the cantilevered members in a fixed relationship to the rib or lip, thereby providing a positive lock.

BRIEF DESCRIPTION OF THE DRAWINGS

FIG. 2 comprises FIGS. 2, 2B and 2C, in which 2 is a perspective side view of the connection device of the invention, 2B is a perspective side view of the securing member and 2C is perspective side view of the locked connector body and connector head assembly. FIGS. 2B and 2C represent an exploded view of FIG. 2A.

FIG. 3 comprises FIGS. 3, 3B and 3C, in which the connector assembly of FIG. 2C is shown turned for detachment, in the case of FIG. 3, and exploded in the case of FIGS. 3B and 3C, to show the component parts of the connector body and connector head.

FIG. 4 comprises FIGS. 4, 4B and 4C which show cross-sectional views along lines 4A—4A of FIG. 2, lines 4B—4B of FIG. 2C and lines 4C—4C of FIG. 3.

FIG. 5 comprises FIGS. 5, 5B and 5C, in which FIG. 5 is a perspective side view of an alternative connector assembly, FIG. 5B is the same view except that it contains a cutaway section showing a locking mechanism and the related unlocking ramped lip, and FIG. 5C is a cross sectional view along line 5C—5C of FIG. 5B.

FIG. 6 comprises FIGS. 6 and 6B, in which FIG. 6 is a perspective, partial exploded view and FIG. 6B is a side view of the connection device of the invention.

DETAILED DESCRIPTION OF THE INVENTION

Figure 1:
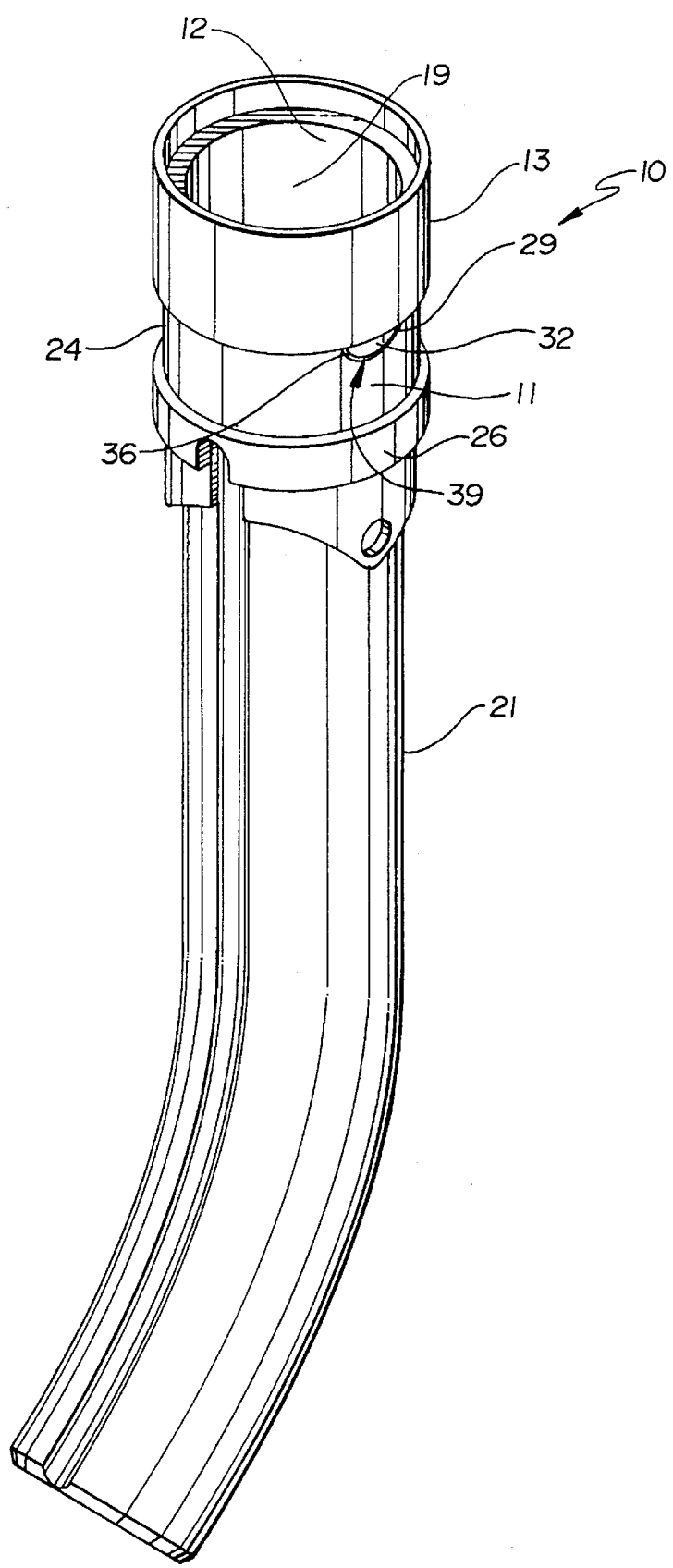
FIG. 1 is a perspective side view of a tracheostomy device embracing the connection device of the invention.

Reference is made to the drawings as an aid to understanding the details of the invention. The numbers used in the drawings are consistently applied and where the same number is employed in more than one figure, it has the same meaning. FIG. 1 shows the relationship of a locking device 10 of the invention to a typical tracheostomy tube assembly. An outer cannula 21 is provided with a connector head 11 circumscribing its end. An inner cannula (not shown) is provided with a connector body 12 circumscribing its end. These components are locked together via locking device 10. Not shown in FIG. 1 or the other drawings is the conventional tubing connecting the breathing apparatus mechanism to the connector head 11 and connector body 12. Such breathing apparatus tubing is generally made of a flexible plastic such as plasticized polyvinylchloride. The tubing is mechanically fitted to breathing apparatus connector 13. It is desirable that the tubing's inside diameter is not less than the largest outer diameter dimension of the connector body 12. Locking device 10 has an open passageway 19 that openly connects with the tubular opening of cannulae and the tubular opening of the breathing apparatus tubing (not shown) that is mechanically fitted to the breathing apparatus connector 13. Open passageway 19 defines a portion of the air passageway to the patient's trachea.

FIG. 2 focuses on the locking device 10. Locking device 10 is composed of three main components: connector head 11, connector body 12 and rib engagement or breathing apparatus connector 13. Locking device 10 is connected to outer cannula 21 of the tracheostomy tube via connector head 11 and inner cannula via connector body 12 and connected to the breathing apparatus via attachment of the breathing apparatus tubing (not shown) to the junction of the two. Connector head 11 has an attachable and detachable relationship with connector body 12. When connector head 11 and connector body 12 are attached, the inner cannula is situated within the outer cannula 21 and a rib engagement or breathing apparatus connector 13, functioning as a collar, slides over the attached connector head 11 and connector body 12 to apply a positive pressure on their juncture, to assure that they are not separated. This design ensures security against accidental disconnections while providing minimum discomfort to the patient when the breathing apparatus connector 13 is removed and the connector body 12 is detached from the connector head 11.

As depicted in FIGS. 2 and 3, connector head 11 and connector body 12 are cylindrical and when they are connected, a part of each is concentrically inter-aligned. Connector body 12 has a cylindrical coupling surface or mating surface 14 and an exposed cylindrical base 16. Base 16 has a larger diameter than coupling surface 14 and the juncture of the two forms seating surface 15. Seating surface 15 circumscribes both exposed base 16 and coupling surface 14.

The shapes of the connector body 12 and connector head 11 may be reversed, e.g., the cylindrical coupling surface 14 and seating surface 15 could be part of connector head 11 and connector head 11 could adopt the shape and function of the remainder of connector body 12 except that it would still be attached to the outer cannula 21, whereas connector body 12 could adopt the shape and function of connector head 11 except that it would still be connected to the inner cannula 20.

As shown in FIGS. 1–4, connector body 12 contains one or more ribs 17o However, if the functions of connector body 12 and connector head 11 were reversed, then each rib 17 would be on connector head 11. The description set forth below is equally applicable to a device wherein the connector head 11 is provided with one or more ribs 17.

One or more ribs 17 extend from seating surface 15 and mating surface 14. Each rib 17 in this embodiment is generally mushroom-shaped, in this case an inverted mushroom shape, with a sloping stem 41 connected to seating surface 15, and sidewalls 42 that mainly connect to surface 14, and a sloping cap 32, extending from stem 41, mated to sidewalls 53 extending from surface 14. The slopes of stem 41 and cap 32 are in the same direction and their variations in thickness, determined along imaginary lines defined as normal to seating surface 15, are substantially the same except where cap 32 extends beyond the dimensions of stem 41. The distance from the top of stem 41 and cap 32 to the mating surface 14 varies depending on the point of measurement so as to form the slope. However, to ensure proper connection to the connector head 11, it is preferred that each rib 17 be no thicker than the distance across seating surface 15.

Sidewalls 42 and 53 are straight or sloping depending on a number of factors. If sidewalls 42 and 53 are intended to provide part of the ramping surface of stem 41 and cap 32, then it is desirable that they have a sloping surface. But if all of the ramping will be provided by the surfaces of stem 41 and cap 32, then sidewalls 42 and 53 may be straight. Preferably, sidewalls 42 and 53 taper away from stem 41 and cap 32. The overall shape of rib 17 may vary consistent with need for a secure connection between connector body 12 and connector head 11. By way of illustration but not limitation, oblong, triangular and fin shaped ribs 17 are contemplated.

Associated with rib 17 and part of cap 32 are two catches 36. Catches 36 appear as the overhang portion of cap 32 and function as hooks. Each catch 36 has a thickness in keeping with the sloping characteristics of cap 32 and sidewalls 53. Where the slope of cap 32 is in one direction, then one catch 36 will be higher than the other catch 36. The lower catch 36 will be part of the ramping surface used for detachment.

As shown in FIGS. 3 and 4, ribs 17 contain sloping surfaces, illustrated in this case as stem 41. Cap 32 is equally sloping. These sloping surfaces provide a ramping surface by which the connector head 11, in this embodiment, can be detached from connection to connector body 12.

In order to latch connector head 11 to connector body 12, there may be provided on connector head 11 one or more latch receiver surfaces 29 within one or more cut-out portions 39 of a sleeve 24. Sleeve 24 emerges from base coupling collar 26. Base coupling collar 26 is bonded, preferably adhesively, to cannula 21. Cut-out portion 39 has the general shape of ribs 17 so that catch 36 may comfortably fit within latch receiving surfaces 29. Latch receiving surfaces 29 form part of the sidewall of sleeve 24. Catch 36 and latch receiving surface 29 form a latch 30 by which connector head 11 and connector body 12 are locked together.

Sleeve 24 is made of a pliable material such as polyester, polycarbonate and polysulfone and expands when twisted so that its inner surface slides over rib 17. This cantilevered action separates catch 36 from latch receiving surfaces 29.

A special feature of rib 17 is the sloping surface which allows ramping of the flexible cantilevered sleeve 24 up and on the uppermost surface of rib 17. When twisted sleeve 24 rides on the uppermost surface of rib 17, catch 36 is fully detached from latch receiving surfaces 29 allowing connector head 11 to be separated from connector body 12 by pulling them apart. Alternatively, as described below, a ramped lip 31 may be provided upon which the cantilevered sleeve 24 slide to detach the catch 36 and latch receiving surfaces 29.

This action of the sleeve 24 ramping up the surface of the rib 17 is illustrated in FIG. 4. FIG. 4 characterizes the relationship of breathing apparatus connector 13 to connector head 11 and connector body 12. As can be seen in FIG. 4, when supporting breathing apparatus connector 13 is slid over mated connector head 11 and connector body 12, connector head 11 is prevented from being twisted in any direction by ribs 17. In this position, receiving surface 29 is locked with catch 36 thereby preventing connector body 12 from being extracted from its position within connector head 11.

Rib 17 possesses a sloping surface which has a minimum height at one edge(s) and a maximum height at about the opposite edge(s). This slope creates a ramping surface which connector head 11 can expand on. This is shown in FIG. 4C. As connector head 11 is twisted to the left, from its position set forth in FIG. 4B, the leading edge of latch receiving surface 29 is allowed to ride up on the minimum height section of the sloping surface of rib 17. Of course, this movement can be done only when breathing apparatus connector 13 has been removed from its position shown in FIG. 4 about the connector head 11 and connector body 12. As illustrated in FIG. 4C, as connector head 11 rides onto the sloping surface of cap 32 and stem 41, cantilevered sleeve 24 expands so that connector head 11 and connector body 12 can be pulled apart.

With respect to FIGS. 5, 5B and 5C, the locking device 10 has a rib 17 and sloping lip 31 around the circumference of mating surface 14. Slope may be gentle or steep. This slope creates a ramping surface which sleeve 24 can expand on as connector body 12 is pulled in a vertical direction away from the connector head 11. When the connector body 12 is pulled away from the connector head 11, catch 36 disengages from latch receiving surface 29 as sleeve 24 expands over lip 31. In this embodiment, rib 17 does not have a ramping surface and functions to communicate with cut out portions 39 of sleeve 24.

As depicted in FIG. 6, cantilevered sleeve 24 may be incorporated into a rigid connector body 12. Catches 36 lock to latch receiving surfaces 29 of connector head 11 to form latch 30 as depicted in FIGS. 6 and 6B. When breathing apparatus connector 13 is provided over connector body 12, sleeve 24 may not expand.

To facilitate securing of catch 36 to latch receiving edges 29, lip 31 may be provided with ascending 67 and descending 68 ramping surfaces upon which are located latch receiving surfaces 29. Catch locking surface 73 is shaped to articulate with ascending 67 and descending 68 ramping surfaces. In locked position, catch locking surface 73 articulates with ascending 67 and descending 68 ramping surfaces. If pressure is exerted such that connector body 12 and connector head 11 are pulled from each other along a vertical axis, catch locking surface 73 rides up ascending surface 67 and down descending surface 68, thereby expanding sleeve 24 and disconnecting catch 36 from latch receiving surfaces 29. However, if breathing apparatus connector 13 is affixed over connector body 12 and connector head 11 when latch 30 is in place, a positive pressure is formed on the sleeve 24, preventing its expansion and ensuring a secure connection.

This device 10 may be constructed from a variety of materials. However, it is preferred that the connector head 11 constructed of polyester, polycarbonate or polysulfone to provide pliability and connector body 12 be constructed of a rigid material such as polypropylene. Other materials, such as ABS® and DELRIN® may be employed.

Although the description of the preferred embodiment has been quite specific, it is contemplated that various modifications may be made without deviating from the spirit of the present invention. Accordingly, it is intended that the scope of the present invention be dictated by the appended claims rather than by the description of the preferred embodiment.

I claim:

1. A tracheostomy tube for insertion into the trachea of a patient to support breathing, comprising:

an outer cannula having a distal end for placement within the trachea and a proximal end for placement outside of the trachea;

a connector head attached to and circumscribing said proximal end of said outer cannula;

a removable inner cannula having a distal end for insertion into said outer cannula and a proximal end for extending outside of said outer cannula; and a connector body attached to and circumscribing said proximal end of said outer cannula and which mates with said connector head when said inner cannula is fully inserted into said outer cannula;

wherein said tracheostomy tube includes a locking device comprising said connector body, said connector head, and a slidable securing means that fits over and about the mated connector body and connector head, in which said connector body and said connector head are locked together by joined catch and a latch receiving surface, said catch is located on one of said connector head or said connector body, and said latch receiving surface is located on the other of said connector head or connector body, to form an interlocking male and female assembly, either said connector body or said connector head is provided with a rib, and whichever of said connector head or said connector body that does not have said rib is provided with at least one flexible cantilevered member capable of mounting said rib and expanding sufficiently that said connector head and said connector body can be connected and separated.

2. The tracheostomy tube of claim 1, wherein said rib has a sloping surface which forms a ramp.

3. The tracheostomy tube of claim 1, wherein said rib has two sides, each side having a slope.

4. A tracheostomy tube for insertion into the trachea of a patient to support breathing, comprising:

an outer cannula having a distal end for placement within the trachea and a proximal end for placement outside of the trachea;

a connector head attached to and circumscribing said proximal end of said outer cannula;

a removable inner cannula having a distal end for insertion into said outer cannula and a proximal end for extending outside of said outer cannula; and a connector body attached to and circumscribing said proximal end of said outer cannula and which mates with said connector head when said inner cannula is fully inserted into said outer cannula;

wherein said tracheostomy tube includes a locking device comprising said connector body, said connector head, and a slidable securing means that fits over and about the mated connector body and connector head, in which said connector body and said connector head are locked together by joined catch and a latch receiving surface, said catch is located on one of said connector head or said connector body, and said latch receiving surface is located on the other of said connector head or connector body, to form an interlocking male and female assembly, said connector body or said connector head being provided with a rib having a cap wherein said catch is located on said rib and whichever of said connector body or said connector head that does not have said rib is provided with at least one flexible cantilevered member capable of mounting said rib and expanding the same sufficiently that said connector body and said connector head can be connected and separated.

5. A tracheostomy tube for insertion into the trachea of a patient to support breathing, comprising:

an outer cannula having a distal end for placement within the trachea and a proximal end for placement outside of the trachea;

a connector head attached to and circumscribing said proximal end of said outer cannula;

a removable inner cannula having a distal end for insertion into said outer cannula and a proximal end for extending outside of said outer cannula; and a connector body attached to and circumscribing said proximal end of said outer cannula and which mates with said connector head when said inner cannula is fully inserted into said outer cannula;

wherein said tracheostomy tube includes a locking device comprising said connector body, said connector head, and a slidable securing means that fits over and about the mated connector body and connector head, in which the connector body and connector head are locked together by joined catch and a latch receiving surface, said catch is located on said connector body and said latch receiving surface is located on said connector head to form an interlocking male and female assembly, said connector body is provided with a rib, and said connector head is provided with a flexible cantilevered member capable of mounting said rib and expanding sufficiently that said connector body and said connector head can be connected and separated.

6. The tracheostomy tube of claim 5 wherein said rib is ramped to facilitate expansion of said flexible cantilevered member when said connector body is rotated over said rib.

7. The tracheostomy tube of claim 6 wherein said rib has two sides, each side comprising a sloping edge.

8. A tracheostomy tube for insertion into the trachea of a patient to support breathing, comprising:

an outer cannula having a distal end for placement within the trachea and a proximal end for placement outside of the trachea;

a connector head attached to and circumscribing said proximal end of said outer cannula;

a removable inner cannula having a distal end for insertion into said outer cannula and a proximal end for extending outside of said outer cannula; and a connector body attached to and circumscribing said proximal end of said outer cannula and which mates with said connector head when said inner cannula is fully inserted into said outer cannula;

wherein said tracheostomy tube includes a locking device comprising said connector body, said connector head, and a slidable securing means that fits over and about the mated connector body and connector head, in which the connector body and connector head are locked together by joined catch and a latch receiving surface, said catch is located one of said connector head or said connector body, and said latch receiving surface is located on the other of said connector head or said connector body, to form an interlocking male and female assembly, either said connector body or said connector head is provided with a lip, and whichever of said connector head or said connector body that does not have the lip is provided with at least one flexible cantilevered member capable of mounting said lip and expanding sufficiently that said connector head and said connector body can be connected and separated.

9. The tracheostomy tube of claim 8 wherein said lip spans the circumference of said connector head or said connector body.

10. The tracheostomy tube of claim 8 wherein said lip has a ramped surface to facilitate expansion of said flexible cantilevered member over said lip when connecting and disconnecting said connector body to said connector head.

11. The tracheostomy tube of claim 8 wherein said lip has a descending and ascending ramped surface to facilitate expansion of said flexible cantilevered member over said lip when connecting and disconnecting said connector body to said connector head.

* * * * *